United States Patent
Rokkam et al.

(10) Patent No.: US 12,234,417 B2
(45) Date of Patent: Feb. 25, 2025

(54) PROCESS FOR SEPARATING CYCLIC PARAFFINS

(71) Applicant: UOP LLC, Des Plaines, IL (US)

(72) Inventors: Ram Ganesh Rokkam, Visakhapatnam (IN); Amit Jain, Mumbai (IN); Ashish Mathur, Gurugram (IN); Nirlipt Mahapatra, Gurugram (IN); Prasenjit Basu Sarkar, NewDelhi (IN); Sourabh Maithil, Gurgaon (IN)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/954,072

(22) Filed: Sep. 27, 2022

(65) Prior Publication Data
US 2023/0183585 A1 Jun. 15, 2023

Related U.S. Application Data

(60) Provisional application No. 63/288,282, filed on Dec. 10, 2021.

(51) Int. Cl.
| | |
|---|---|
| *C10G 61/02* | (2006.01) |
| *C10G 63/04* | (2006.01) |
| *C10G 69/08* | (2006.01) |

(52) U.S. Cl.
CPC ............ *C10G 61/02* (2013.01); *C10G 63/04* (2013.01); *C10G 69/08* (2013.01); *C10G 2300/4081* (2013.01); *C10G 2400/20* (2013.01)

(58) Field of Classification Search
CPC ........ C10G 61/02; C10G 63/04; C10G 69/08; C10G 2300/4081; C10G 2400/20
See application file for complete search history.

(56) References Cited

U.S. PATENT DOCUMENTS 2,370,412 A * 2/1945 Morris .................... C10G 57/00
585/326
3,211,797 A * 10/1965 Houston, Jr. ........... C07C 15/04
585/405

(Continued)

FOREIGN PATENT DOCUMENTS

| CN | 103483128 A | 1/2014 |
| EP | 2909159 B1 | 9/2016 |

OTHER PUBLICATIONS

Doherty et al. ("Distillation." Chap. 13.0 in Perry's Chemical Engineers' Handbook. 7th ed., 2008) (Year: 2008).*

(Continued)

*Primary Examiner* — Jonathan Miller
*Assistant Examiner* — Jason Y Chong
(74) *Attorney, Agent, or Firm* — Paschall & Associates, LLC; James C. Paschall

(57) ABSTRACT

A feed stream of cyclic paraffins may be separated to obtain an overhead of methylcyclopentane or cyclohexane and a bottoms stream cyclohexane or methylcyclohexane. The overhead stream may be subjected to separation of normal paraffins from non-normal paraffins with the former being isomerized or the entire overhead stream may be isomerized. In a further embodiment, the bottoms stream may be subjected to steam cracking. In an additional embodiment, the feed stream of cyclic paraffins may be formerly subjected to aromatic saturation.

16 Claims, 1 Drawing Sheet

(56) References Cited

U.S. PATENT DOCUMENTS

| | | | | |
|---|---|---|---|---|
| 3,406,217 A | * | 10/1968 | Davison | C10G 69/06 |
| | | | | 208/92 |
| 2005/0101819 A1 | * | 5/2005 | Galperin | B01J 29/06 |
| | | | | 502/263 |
| 2007/0062848 A1 | | 3/2007 | Oballa et al. | |
| 2019/0359541 A1 | * | 11/2019 | Bafna | C10G 69/14 |
| 2021/0276933 A1 | | 9/2021 | Koseoglu | |
| 2021/0277316 A1 | | 9/2021 | Funk et al. | |

OTHER PUBLICATIONS

Zimmermann et al. ("Ethylene." In Ullmann's Encyclopedia of Industrial Chemistry, 2009, https://doi.org/10.1002/14356007.a10_045 .pub3) (Year: 2009).*

Search Report and Written Opinion for PCT/US2022/081004 dated Apr. 17, 2023.

* cited by examiner

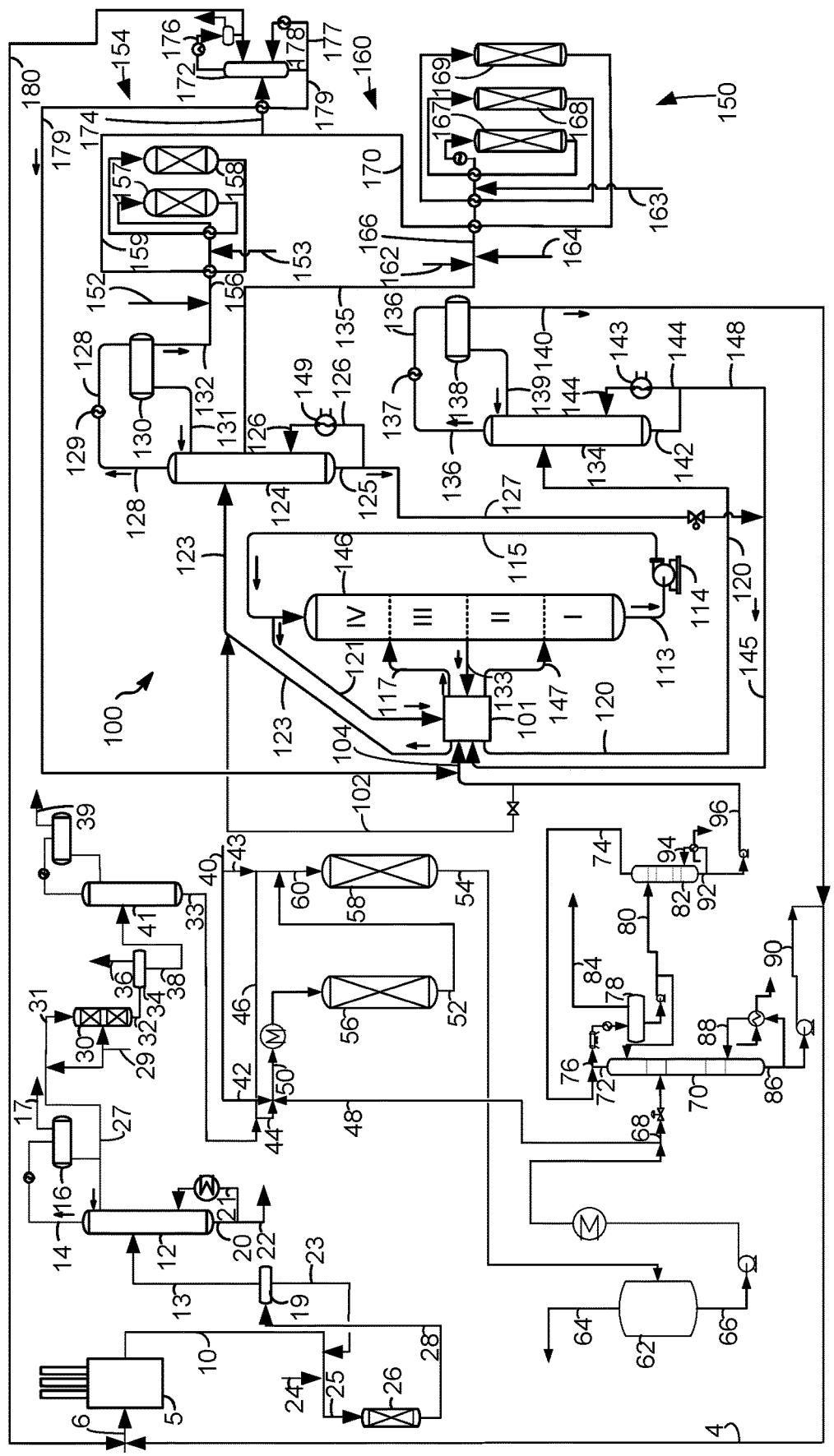

PROCESS FOR SEPARATING CYCLIC PARAFFINS

CROSS-REFERENCE TO RELATED APPLICATIONS

This application claims priority from U.S. Provisional Application No. 63/288,282, filed Dec. 10, 2021, which is incorporated herein in its entirety.

FIELD

The field is processes for separating cyclic paraffins and particularly for increasing the concentration of naphthenes in a feed stream.

BACKGROUND

Ethylene and propylene are important chemicals for use in the production of other useful materials, such as polyethylene and polypropylene Polyethylene and polypropylene are two of the most common plastics found in use today and have a wide variety of uses. Uses for ethylene and propylene include the production of vinyl chloride, ethylene oxide, ethylbenzene and alcohol.

The great bulk of the ethylene consumed in the production of the plastics and petrochemicals such as polyethylene is produced by the thermal cracking of hydrocarbons. Steam is usually mixed with the feed stream to the cracking furnace to reduce the hydrocarbon partial pressure and enhance olefin yield and to reduce the formation and deposition of carbonaceous material in the cracking reactors. The process is therefore often referred to a steam cracking or pyrolysis.

Steam cracking generates less valuable by-products such as pyrolysis gas (pygas) and fuel oil. Pygas contains large proportions of paraffins and aromatics. Paraffins can be recovered or further processed to prepare useful steam cracking feed. Aromatics are a very poor steam cracking feed because they typically increase the yield of low-value fuel oil.

An efficient process for managing aromatics in a pygas feed is needed for improving the value of steam cracking units.

BRIEF SUMMARY

The disclosed process provides for obtaining a stream highly concentrated in cycloparaffins. A feed stream of cyclic paraffins may be separated to obtain an overhead of methylcyclopentane or cyclohexane and a bottoms stream cyclohexane or methylcyclohexane. In an embodiment, the overhead stream can be subjected to separation of normal paraffins from non-normal paraffins with the former being isomerized or the entire overhead stream may be isomerized. In a further embodiment, the bottoms stream can be subjected to steam cracking. In an additional embodiment, the feed stream of cyclic paraffins may be formerly subjected to aromatic saturation.

Additional details and embodiments of the disclosure will become apparent from the following detailed description of the disclosure.

BRIEF DESCRIPTION OF THE DRAWINGS

The FIG. 1s a schematic view of a conversion unit of the present disclosure.

Definitions

The term "communication" means that fluid flow is operatively permitted between enumerated components, which may be characterized as "fluid communication". The term "communication" may also mean that data or signals are transmitted between enumerated components which may be characterized as "informational communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "a component-rich stream" means that the rich stream coming out of a vessel has a greater concentration of the component than the feed to the vessel.

As used herein, the term "a component-lean stream" means that the lean stream coming out of a vessel has a smaller concentration of the component than the feed to the vessel.

As used herein, the term "boiling point temperature" means atmospheric equivalent boiling point (AEBP) as calculated from the observed boiling temperature and the distillation pressure, as calculated using the equations furnished in ASTM D 1160 appendix A7 entitled "Practice for Converting Observed Vapor Temperatures to Atmospheric Equivalent Temperatures".

As used herein, the term "True Boiling Point" (TBP) means a test method for determining the boiling point of a material which corresponds to ASTM D-2892 for the production of a liquefied gas, distillate fractions, and residuum of standardized quality on which analytical data can be obtained, and the determination of yields of the above fractions by both mass and volume from which a graph of temperature versus mass % distilled is produced using fifteen theoretical plates in a column with a 5:1 reflux ratio.

As used herein, the term "T5" or "T95" means the temperature at which 5 mass percent or 95 mass percent, as the case may be, respectively, of the sample boils using ASTM D-86 or TBP.

As used herein, the term "initial boiling point" (IBP) means the temperature at which the sample begins to boil using ASTM D-7169, ASTM D-86 or TBP, as the case may be.

As used herein, the term "end point" (EP) means the temperature at which the sample has all boiled off using ASTM D-7169, ASTM D-86 or TBP, as the case may be.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

As used herein, the term "predominant" or "predominate" means greater than 50%, suitably greater than 75% and preferably greater than 90%.

The term "Cx" is to be understood to refer to molecules having the number of carbon atoms represented by the subscript "x". Similarly, the term "Cx−" refers to molecules that contain less than or equal to x and preferably x and less carbon atoms. The term "Cx+" refers to molecules with more than or equal to x and preferably x and more carbon atoms.

DETAILED DESCRIPTION

We have found that methylcyclopentane is a poor steam cracking feed. On the other hand, cyclohexane is a very good steam cracking feed which cracks to ethylene and butadiene, two valuable petrochemicals. We propose to separate a cycloparaffinic feed stream into a methylcyclopentane rich stream and a cyclohexane rich stream and isomerize the methylcyclopentane rich stream while steam cracking the cyclohexane rich stream. Moreover, if the operator prefers to make more ethylene and propylene than butadiene, we alternatively propose to separate the cycloparaffinic feed stream into a cyclohexane rich stream and a methylcyclohexane rich stream and to isomerize the methylcyclohexane rich stream and steam crack the methylcyclohexane rich stream. The cycloparaffinic feed stream may be an effluent from an aromatic saturation unit.

Turning to FIG. 1 of the present process, a pyrolysis feed stream in line 6 which may receive a recycle extract stream in line 4 and an isomerate overhead stream in line 180 is steam cracked in a steam cracking unit 5 to produce several pyrolysis streams. A pyrolysis stream in pyrolysis line 10 predominantly comprises C5+ hydrocarbons. The pyrolysis stream in line 10 may be subjected to selective hydrogenation before it is ready for saturation. The pyrolysis stream in line 10 may be subjected to selective hydrogenation to convert diolefins and conjugated-diolefins in the pyrolysis line 10 to monoolefins. A recycle stream in line 23 and hydrogen from a hydrogen line 24 is added to the pyrolysis stream in line 10 and a resulting combined pyrolysis stream in line 25 is charged to a selective hydrogenation reactor 26. The selective hydrogenation reactor 26 is normally operated at relatively mild hydrogenation conditions. The reactants will normally be maintained under the minimum pressure sufficient to maintain the reactants as liquid phase hydrocarbons. A broad range of suitable operating pressures therefore extends from about 276 kPa(g) (40 psig) to about 5516 kPa(g) (800 psig), or about 345 kPa(g) (50 psig) to about 3795 kPa(g) (550 psig). A relatively moderate temperature between about 25° C. (77° F.) and about 350° C. (662° F.), or about 50° C. (122° F.) and about 150° C. (302° F.) is typically employed. The liquid hourly space velocity of the reactants through the selective hydrogenation catalyst should be about 1.0 $hr^{-1}$ and about 35.0 $hr^{-1}$. To avoid the undesired saturation of a significant amount monoolefinic hydrocarbons, the mole ratio of hydrogen to diolefinic hydrocarbons in the material entering the bed of selective hydrogenation catalyst is maintained between 0.75:1 and 2.5:1.

Any suitable catalyst which is capable of selectively hydrogenating diolefins in a naphtha stream may be used. Suitable catalysts include, but are not limited to, a catalyst comprising platinum, palladium, copper, titanium, vanadium, chrome, manganese, cobalt, nickel, zinc, molybdenum, and cadmium or mixtures thereof. The metals are preferably supported on inorganic oxide supports such as silica and alumina, for example.

The selectively hydrogenated pyrolysis stream in line 28 is separated in a separator 19 to provide the recycle stream in a bottoms line 23 and a vaporous pyrolysis stream in an overhead line 13 which is fed to a pyrolysis fractionation column 12.

The vaporous pyrolysis stream in line 13 may be preliminarily fractionated in a pyrolysis fractionation column 12 to remove C9+ hydrocarbons. Light olefins preferably are removed from the pyrolysis stream in line 10 in a steam cracking light olefin recovery section prior to selective hydrogenation and pyrolysis fractionation. The pyrolysis fractionation column 12 is operated to separate an off gas stream in line 17 comprising C4− hydrocarbons wet gas, a net overhead stream comprising C5-C8 hydrocarbons pyrolysis product in a net overhead line 27, rich in benzenes, toluene and xylenes, and a pyrolysis bottoms stream rich in C9+ hydrocarbons in line 20. The pyrolysis overhead stream is withdrawn from the pyrolysis fractionation column 12 in an overhead line 14, condensed in a cooler and fed to a separator 16. A portion of the condensed pyrolysis overhead stream is recycled to the pyrolysis fractionation column 12 as reflux through a reflux line and the remaining portion of the condensed net pyrolysis overhead stream is withdrawn through a net pyrolysis overhead line 27. Wet gases are withdrawn in the off gas line 17 while the C5-C8 hydrocarbon pyrolysis product is withdrawn in the net overhead line 27.

The pyrolysis bottoms stream is withdrawn from pyrolysis fractionation column 12 through a bottoms line 20 where a portion of the pyrolysis bottoms stream flows through a reboiler line 21 to a reboiler heater and returns heated to the pyrolysis fractionation column 12. A net pyrolysis bottoms stream flows through line 22 rich in C9+ hydrocarbons which may be recovered or further processed. The pyrolysis fractionation column 12 operates in bottoms temperature range of about 225 to about 275° C. and an overhead pressure of about 250 to about 350 kPa (gauge).

The combined pyrolysis product stream in line 31 may be heated and charged to the hydrotreating reactor 30. The hydrotreating reactor 30 may have one or more beds of hydrotreating catalyst to hydrodemetallate, hydrodenitrogenate and hydrodesulfurize the combined selectively hydrogenated pyrolysis stream. The combined pyrolysis product stream may be charged to the hydrotreating reactor 30 at a hydrotreating inlet temperature that may range from about 200° C. (392° F.) to about 400° C. (752° F.). The hydrotreating reactor 30 may employ interbed hydrogen quench streams from the hydrogen manifold 29.

Suitable hydrotreating catalysts are any known conventional hydrotreating catalysts and include those which are comprised of at least one Group VIII metal, preferably iron, cobalt and nickel, more preferably cobalt and/or nickel and at least one Group VI metal, preferably molybdenum and tungsten, on a high surface area support material, preferably alumina. Other suitable hydrotreating catalysts include zeolitic catalysts, as well as noble metal catalysts where the noble metal is selected from palladium and platinum. It is within the scope of the present description that more than one type of hydrotreating catalyst be used in the same hydrotreating reactor 30. The Group VIII metal is typically present in an amount ranging from about 2 to about 20 wt %, preferably from about 4 to about 12 wt %. The Group VI metal will typically be present in an amount ranging from about 1 to about 25 wt %, preferably from about 2 to about 25 wt %. Generally, hydrotreating conditions include a pressure of about 700 kPa (100 psig) to about 21 MPa (3000 psig). The hydrotreating outlet temperature may range between about 300° C. (572° F.) and about 427° C. (800° F.).

The hydrotreated effluent stream may exit the hydrotreating reactor in line 32 and enter a hydrotreating separator 34 to provide an overhead stream rich in hydrogen in line 36 that may be scrubbed (not shown) to remove hydrogen sulfide and ammonia or other compounds and compressed and returned back to the hydrogen line 24 after perhaps supplementation with a make-up hydrogen stream. A hydrotreated pyrolysis stream is provided from a bottoms line 38 from the hydrotreater separator 34 and stripped in a stripper column 41 to remove C4– off gases in a stripper off-gas line 39 and a stripped pyrolysis stream in a stripper bottoms line 33.

The stripped pyrolysis stream may in line 33 is rich in C6-C8 aromatics. In an embodiment, the preliminary overhead feed comprises at least about 5 to about 10 wt % C6-C8 aromatics. The stripped pyrolysis stream may have the composition shown in Table 1.

TABLE 1

| COMPONENT | wt % |
| --- | --- |
| Isopentane | 3-7 |
| N-Pentane | 5-9 |
| Cyclopentane | 5-10 |
| N-Hexane | 1-5 |
| Cyclohexane | 4-9 |
| Benzene | 20-40 |
| N-Heptane | 0.1-1 |
| Methylcyclohexane | 0.5-3 |
| Toluene | 10-30 |
| 1,1-Dimethylcyclohexane | 0.5-3 |
| Ethylbenzene | 2-12 |
| Xylenes | 2-10 |
| C9+ | 1-5 |
| Total Aromatics | 34-92 |

The pyrolysis stream may comprise about 12 to about 26 wt % pentanes, about 5 to about 14 wt % hexane, about 20 to about 40 wt % benzene, about 0.6 to about 4 wt % heptanes, about 10 to about 30 wt % toluene, about 2 to about 12 wt % ethylbenzene, about 2 to about 10 wt % xylenes and about 34 to about 92 wt % total aromatics.

The hydrotreated pyrolysis stream in line 33 may be heated and processed through sulfur guard beds to remove sulfur to less than 0.1 wppm and pumped to the saturation reactor pressure of about 1.7 MPa (250 psig) to about 4.5 MPa (650 psig) by a charge pump.

The pyrolysis stream in line 33 may be split into at least a first pyrolysis stream in line 44 and a second pyrolysis stream in line 46 each for a dedicated saturation reactor. This arrangement can maintain the exotherm for each saturation reactor below 200° C. (360° F.), preferably below 111° C. (200° F.). To reduce the tendency for side reactions, a hydrogen stream in line 40 is split into a number of streams, perhaps like the number of multiple pyrolysis streams, each dedicated to a single saturation reactor. The hydrogen stream in line 40 entering the process may be split into a first hydrogen stream in line 42 and a second hydrogen stream in line 43. The first hydrogen stream in line 42 may be added to the first pyrolysis stream in line 44. The second hydrogen stream in line 43 may be added to the second pyrolysis stream in line 46. For systems using a platinum-based catalyst, the hydrogen should be very pure make-up hydrogen, preferably from a pressure-swing adsorption unit, with no more than about 1 mole-ppm carbon monoxide.

The first pyrolysis stream in line 44 may comprise about 5 to about 50 vol-% and typically about 30 to about 50 vol-% of the hot desulfurized pyrolysis stream in line 42. The second pyrolysis stream in line 46 may comprise the balance. The first hydrogen stream in line 42 may be added to the first pyrolysis stream in line 44. Moreover, to further manage the saturation exotherm a recycle stream in line 48 may be added to the first pyrolysis stream in line 44 to provide a first combined charge stream in line 50. The recycle stream may be taken from a first saturated effluent stream in line 52 or a second saturated effluent stream in line 54, the latter being preferred. The first combined charge stream in line 50 may be heated to about 120° C. (248° F.) to about 230° C. (446° F.) and charged to the first saturation reactor 56.

In the first saturation reactor 56, aromatics are saturated over a bed of saturation catalyst to naphthenes to provide a first saturated effluent stream. The saturation catalyst may be the same in both saturation reactors 56 and 58. The saturation catalyst may comprise a noble metal, platinum or palladium, a platinum-lithium or nickel on a porous carrier material or any know commercial hydrogenation catalyst.

The porous carrier material may have a surface area of about 25 to about 500 square meters per gram, preferably about 150 to about 225 square meters per gram, and may comprise non-acidic, amorphous alumina. Gamma alumina may be preferred. In addition, a preferred alumina will have an apparent bulk density of about 0.30 to about 0.70 gm/cc and surface area characteristics such that the average pore diameter is about 20 to about 300 Angstroms and the pore volume is about 0.10 to about 1.0 milliliter per gram. The alumina carrier may be prepared by adding a suitable alkaline reagent, such as ammonium hydroxide, to a salt of aluminum, such as aluminum chloride, or aluminum nitrate, in an amount to form an aluminum hydroxide gel which, upon drying and calcination, is converted to alumina. The carrier material may be formed in any desired shape such as spheres, pills, cakes, extrudates, powders, granules, etc., and may further be utilized in any desired size.

The Group VIII noble metal component, for example platinum, may exist within the final catalytic composite as a compound such as an oxide, sulfide, halide, or in an elemental state. The Group VIII noble metal component generally comprises about 0.01% to about 2.0% by weight of the final composite, calculated on an elemental basis. The Group VIII noble metal component may be incorporated within the catalytic composite in any suitable manner including co-precipitation or cogellation with the carrier material, ion-exchange, or impregnation. Following impregnation, the composite may generally be dried at a temperature of about 93° C. (200° F.) to about 204° C. (400° F.), for a period of from 2 to about 24 hours, or more, and finally calcined at a temperature of about 371° C. (700° F.) to about 538° C. (1000° F.), in an atmosphere of air, for a period of about 0.5 to about 10 hours.

In order to avoid side reactions which results in the loss of naphthenes, an alkalinous metal component may be combined with the catalytic composite in an amount of from 0.01% to about 1.5% by weight. This component is selected from the group of alkali metals, particularly lithium and/or potassium.

The saturation catalyst may be reduced in a water-free environment after calcination to reduce the noble metal component. Moreover, the saturation catalyst may be pre-sulfided such as in the presence of hydrogen sulfide to activate the catalyst.

A first saturated effluent stream exits the first saturation reactor 56 in the first saturated effluent line 52 with a greater concentration of naphthenes and a lower concentration of aromatics than in the first combined charge stream in line 50. The first saturated effluent stream in line 52 may be cooled.

The second hydrogen stream in line 43 is added to the second pyrolysis stream in line 46. Moreover, to manage the exotherm in the second saturation reactor 58, the cooled first saturated effluent stream in line 52 is also added to the second pyrolysis stream in line 46 to provide a second combined charge stream in line 60. The second combined charge stream in line 60 may be at a temperature of about 120° C. (248° F.) to about 230° C. (446° F.) and charged to the second saturation reactor 58.

In the second saturation reactor 58 aromatics are saturated over a bed of saturation catalyst to naphthenes to provide a second saturated effluent stream. The saturation catalyst may be the same in both saturation reactors 56 and 58. The saturation catalyst may comprise a porous carrier material having combined therewith a Group VIII noble metal component or any commercial hydrogenation catalyst as described for the first saturation reactor 56.

Conditions in the saturation reactors 56 and 58 should include a hydrogen to hydrocarbon mole ratio of about 0.01 to about 2, preferably about 0.025 to about 0.5 at the reactor outlet, an outlet reaction temperature of about 240° C. (464° F.) to about 400° C. (752° F.), preferably about 250° C. (482° F.) to about 280° C. (536° F.), a LHSV of about 1 to about 50 hr$^{-1}$, preferably, about 15 to about 25 hr$^{-1}$ and a reactor pressure at the last reactor outlet of 1.4 MPa (200 psig) to about 5.6 MPa (800 psig), preferably about 2.1 MPa (300 psig) to about 3.5 MPa (600 psig). The saturation reactors 56 and 58 may be operated in a downflow mode although other reactor configurations and flow regimes may be suitable.

A second saturated effluent stream exits the second saturation reactor 58 in the second saturated effluent line 54 with a greater concentration of naphthenes and a lower concentration of aromatics than in the second combined charge stream in line 60. The second saturated effluent stream in line 54 may be cooled and condensed before it is fed to a separator 62. It is envisioned that a third or additional saturation reactors can be employed.

The cooled second saturated effluent stream in line 54 may be separated into a vapor saturated stream in an overhead line 64 extending from an overhead of the separator 62 and a liquid saturated stream in bottoms line 66 extending from a bottom of the separator 62. The vapor saturated stream in line 64 is rich in hydrogen and may be recycled to line 40 for recycle to the saturation reactors 56 and 58 perhaps with a purge or forwarded to a pressure swing adsorption unit or other unit for hydrogen recovery or to provide make-up gas for any unit. The liquid saturated stream is pumped in the bottoms line 66 and heated and split into the recycle stream in line 48 and a separator fractionator feed stream in line 68. The separator 62 is operated at about 38° C. (100° F.) to about 66° C. (150° F.) and about 2.1 MPa (300 psig) to about 3.1 MPa (450 psig).

The recycle stream in line 48 may be taken from the liquid saturated stream in line 66, heated and added to the first pyrolysis stream in line 44 and the first hydrogen stream in line 42 to provide the first combined charge stream in line 50 charged to the first saturation reactor 56. It is also envisioned that the recycle stream in line 48 may be recycled to the first pyrolysis stream in line 44 and/or to the second pyrolysis stream in line 46. The recycle-to-feed ratio can be about 0 to about 4 and suitably about 0.5 to about 1.5.

The separator fractionator feed stream in line 68 taken from the liquid saturated stream in line 66 is fed to the separator fractionation column 70. The separator fractionation feed stream in line 68 may be separated in the separator fractionation column 70 to provide a separator overhead stream and a separator bottoms stream, preferably by fractionation. In one embodiment, the separator fractionation column 70 may be operated to separate two fractions, a separator overhead stream rich in methylcyclopentane and normal hexane and particularly rich in paraffins and a separator bottoms stream rich in cyclohexane and particularly rich in naphthenes in which the split is taken between normal hexane and cyclohexane. In another embodiment, the separator fractionation column 70 may be operated to separate two fractions, a separator overhead stream rich in methylcyclopentane, normal hexane and cyclohexane and particularly rich in paraffins and a separator bottoms stream rich in methylcyclohexane and particularly rich in naphthenes in which the split is taken between normal hexane and methylcyclohexane.

The separator overhead stream is withdrawn from the separator fractionation column 70 in an overhead line 72 extending from an overhead of the column. A stripper overhead stream in line 74 may be added to the separator overhead stream in line 72 to provide a combined overhead stream in line 76. The combined overhead stream in line 76 may be condensed in a cooler and fed to a separator overhead separator 78. A portion of the condensed separator overhead stream is recycled to the separator fractionation column 70 as reflux through a reflux line and the remaining portion of the condensed separator overhead stream is withdrawn through a net separator overhead line 80. In one embodiment, the condensed separator overhead stream may be forwarded to the steam cracking unit 5. In another embodiment, the condensed separator overhead separator stream may be fed to the overhead liquid stripper 82 to strip out lights. Hydrogen and C3– hydrocarbons are withdrawn in a net separator vapor line 84 from an overhead of the separator overhead receiver 78 and may be transported to a fuel gas header.

The separator bottoms stream is withdrawn from the separator fractionation column 70 in a bottoms line 86 extending from a bottom of the column. A reboil portion of the separator bottoms stream flows through a reboiler line 88, a reboiler heater which may include heat exchange with steam and returns heated to the separator fractionation column 70. A net separator bottoms stream flows through line 90 rich in naphthenes which may be cooled and charged back to the steam cracking unit 5 to produce more light olefins. When the separator bottoms stream is rich in cyclohexane, the pyrolysis product slate will be biased toward more ethylene and butadiene. However, when the separator bottom stream is rich in methylcyclohexane, the pyrolysis product slate will be biased toward more ethylene and propylene because more of the naphthenes will be directed from the separator overhead stream in line 72 to isomerization to produce normal paraffins that will be steam cracked. The separator fractionation column 70 operates in bottoms temperature range of about 110° C. (230° F.) to about 196° C. (385° F.) and an overhead pressure of about 35 kPa to about 700 kPa (gauge).

The condensed separator overhead stream in the net separator overhead line 80 may be stripped in the overhead liquid stripper 82 to assure that light hydrocarbons and hydrogen are removed from the separator overhead stream. The condensed separator overhead stream is stripped into two streams: a stripper overhead stream rich in C3-hydrocarbons and hydrogen and a stripped separator overhead stream rich in C4+ hydrocarbons. The stripper overhead stream is withdrawn in the stripper overhead line 74 extending from an overhead of the overhead liquid stripper and is combined with the separator fractionator overhead stream in line 72 to have C3– hydrocarbons removed from both streams together in the combined overhead stream in line 76.

The stripped separator overhead stream is withdrawn from overhead liquid stripper column 82 in a stripper bottoms line 92 extending from a bottom of the column. A reboil portion of the stripped separator overhead stream flows through a reboiler line 94, a reboiler heater which may include heat exchange with steam and returns heated to the overhead liquid stripper column 82. A net stripped separator overhead stream flows through line 96 rich in lighter naphthenes and paraffins. The overhead liquid stripper column 82 operates in bottoms temperature range of about 55° C. (131° F.) to about 138° C. (280° F.) and an overhead pressure of about 35 kPa to about 700 kPa (gauge).

The separator overhead stream in line 72 comprises the bulk of the naphtha range paraffins and cyclopentane in the first embodiment and cyclohexane in the second embodiment. These naphtha molecules can be isomerized to normal naphtha molecules which are excellent feed in the steam cracker 5. If the stripped separator overhead stream in the stripper bottoms line 96 has at least 5 wt % normal paraffins, preferably at least 10 wt % normal paraffins, it should be directed to the paraffin separation unit 100 that separates non-normal paraffins from normal paraffins to provide a normal paraffin rich stream in line 140 that can be routed to the stream cracking unit 5 as excellent steam cracker feed. If the separator overhead stream in the overhead line 72 has less than 5 wt % normal paraffins, preferably less than 10 wt % normal paraffins, it should bypass the paraffin separation unit 100 in line 102 through a control valve thereon and enter the isomerization unit 160 perhaps through the raffinate splitter column 124 to convert iso-paraffins to normal paraffins to provide a superb steam cracker feed.

The stripped separator overhead stream in bottoms line 96 may be a light naphtha stream comprising substantial naphthenes comprising C4 to C7 paraffins having a T0 between about 40° C. and about 90° C. Suitably no more than about 30 wt % C7+ hydrocarbons, preferably no more than about 20 wt % C7+ hydrocarbons and more preferably no more than about 10 wt % C7+ hydrocarbons can be present in the light naphtha stream. The naphtha feed stream may comprise normal paraffins, iso-paraffins, naphthenes, and aromatics.

Normal paraffins yield more light olefins in a steam cracking unit. Hence, it is desired to increase the concentration of normal paraffins in the stripped separator overhead stream in the bottoms line 96 by separating the naphtha feed stream into a normal paraffin-rich stream and a non-normal paraffin-rich stream by adsorption.

The stripped separator overhead stream in line 96 less any bypassed stream in line 102 and supplemented by a recycle stream in line 179 is passed in an adsorption feed line 104 through a valve 101 in the normal paraffins separation unit 100 which delivers the feed to an appropriate bed in an adsorbent vessel 146. Normal paraffins of the naphtha mixture selectively enter or occlude into the porous structure of the adsorbent components but branched or cyclic non-normal chain paraffins do not typically enter the pores. The non-normal paraffins exit the process as a raffinate stream. The butanes are separated in the adsorption separation unit 100 like the C5-C7 hydrocarbons.

To provide a useful method for separation of normal from non-normal paraffins, it is necessary to desorb the occluded normal paraffins. In the disclosed process, normal nonane or normal decane or even heavier normal paraffin can suitably be used as a desorbent to desorb normal paraffins in an extract-desorbent stream. The adsorbent used in the adsorption vessel preferably comprises aluminosilicate molecular sieves having relatively uniform pore diameters of about 5 Angstroms. The preferred adsorbent is provided by commercially available type 5A molecular sieves produced and sold by UOP LLC in Des Plaines, Illinois.

The adsorbent vessel 146 may comprise a series of vertically spaced, separate beds interconnected by a pipe 115 between the bottom of one bed and the top of its downstream adjacent bed. The valve 101 may comprise a manifold arrangement or a rotary valve for advancing the points of inlet and outlet of respective streams in a downstream direction. The adsorbent vessel 146 operates in a downflow mode, although upflow may be suitable. The adsorbent vessel 146 is shown to have four main zones I-IV for simplicity, though these zones may be further subdivided when accounting for different flushing schemes. The overall process may have other numbers of beds, such as eight, twelve or twenty-four beds, divided among the four main zones I-IV.

The feed stream is introduced through the adsorption feed line 104 through valve 101 which is positioned to send the feed stream through line 147 into the adsorbent vessel 146 between Zones I and II. The extract is withdrawn between Zones II and III in line 133, transported through the valve 101 in an extract line 120 to an extract fractionation column 134 to separate desorbent from extract. The desorbent is introduced through desorbent line 145 through the valve 101 which is positioned to send the desorbent through a desorbent line 117 into the process between Zones III and IV. The raffinate is withdrawn between Zones IV and I through a raffinate line 121, through the valve 101 and through line 123 to the raffinate fractionation column 124.

Simulated countercurrent flow is achieved by periodically advancing downstream the introduction point of the feed stream and the desorbent stream while simultaneously and equally advancing downstream the withdrawal point of the raffinate stream and the extract stream. The Zone I is defined as the zone bounded between the feed stream inlet and the raffinate outlet; the Zone II is defined as the zone bounded between the extract stream outlet and the desorbent inlet; the Zone III is defined as the zone bounded between the desorbent inlet and the extract outlet; and the Zone IV is defined as the zone bounded between the raffinate stream outlet and the desorbent stream inlet. Typical liquid phase operation is preferred, for example, at temperatures from about 50° C. to about 300° C., and more particularly no more than about 260° C., and pressures from slightly super atmospheric to about 30 atmospheres.

Raffinate, characterized as less adsorbed in the adsorption vessel, is withdrawn from the adsorption vessel 146 in the raffinate line 121 through the valve 101 and enters the raffinate fractionation column 124 through line 123. The raffinate stream in line 123 can be considered a non-normal paraffin stream. Since it is desired to obtain a normal paraffin product, the raffinate fractionation column 124 is operated to separate two fractions, a raffinate overhead stream rich in non-normal paraffins, in an embodiment, rich in C7− non-normal paraffins, and a desorbent bottoms stream rich in normal paraffin desorbent, in an embodiment, rich in C9+ normal paraffins. In an additional embodiment, the raffinate feed stream is split into three streams: a raffinate overhead stream in the raffinate overhead line 128 rich in non-normal butanes and perhaps pentanes, a raffinate side stream in a side line 135 from the raffinate fractionation column 124 that is rich in C5 to C7 non-normal paraffins, and a desorbent stream in line 125 rich in C9+ paraffins. The raffinate overhead stream is withdrawn from the raffinate fractionation column 124 in an overhead line 128, condensed in a cooler 129 and fed to a separator 130. A portion of the condensed raffinate overhead is recycled to the raffinate fractionation column 124 as reflux through a reflux line 131 and the remaining portion of the condensed raffinate overhead is withdrawn through a net raffinate overhead line 132. The raffinate overhead stream is rich in C7− isoparaffins which can be transported to the isomerization unit 150.

The raffinate bottoms stream is withdrawn from the raffinate fractionation column 124 through a bottoms line 125 where a portion of the raffinate bottoms stream flows through a reboiler line 126, reboiler heater 149 and returns heated to the raffinate fractionation column 124. The remaining portion of said raffinate bottoms stream flows through a net bottoms line 127 as a normal paraffin rich stream, particularly rich in normal C9+ paraffins. The raffinate bottoms stream comprising a raffinate desorbent stream in line 127 can be recycled to the adsorption vessel 146 in the desorbent line 145 perhaps after joining an extract bottoms stream in line 148. The raffinate fractionation column 124 operates in a bottoms temperature range of about 250 to about 290° C. and an overhead pressure of about 450 to about 550 kPa (gauge).

Extract is more selectively adsorbed on the adsorbent in the adsorption vessel 146. The desorbent displaces the selectively adsorbed normal paraffins from the solid adsorbent in desorbent bed III of adsorbent vessel 146. The extract and desorbent are withdrawn in line 133, and the valve 101 connects line 133 with line 120. Extract and desorbent withdrawn from the adsorption vessel in the extract line 133 connected through the valve 101 is directed in line 120 to the extract fractionation column 134. Since it is desired to obtain a normal paraffin product, the extract fractionation column 134 is operated to separate two fractions, an extract overhead stream rich in normal paraffins, in an embodiment, rich in C4-C7 normal paraffins, and a desorbent bottoms stream rich in normal paraffin desorbent, in an embodiment, rich in C9+ normal paraffins. The extract overhead stream is withdrawn from the extract fractionation column 134 in an overhead line 136, condensed in a cooler 137 and fed to a separator 138. A portion of the condensed extract overhead is recycled to the extract fractionation column 134 as reflux through a reflux line 139 and the remaining portion of the condensed extract overhead is withdrawn through a net extract overhead line 140. The extract overhead stream is rich in C4-C7 normal paraffins which can be recovered or taken as steam cracking unit feed and fed to the steam cracking unit 150 perhaps via steam feed line 4.

The extract bottoms stream is withdrawn from extract fractionation column 134 through a bottoms line 142 where a portion of the extract bottoms stream flows through a reboiler line 144, reboiler heater 143 and returns heated to the extract fractionation column 134. A remaining portion of the extract bottoms stream flows through line 148 as a normal paraffin rich stream, particularly rich in normal C9+ paraffins. The extract bottoms stream in line 148 comprising an extract desorbent stream can join the raffinate bottoms stream in line 127 comprising a raffinate desorbent stream. Both can be recycled in the desorbent line 145 through the valve 101 to the adsorption vessel 146 in the desorbent line 147. The extract fractionation column 134 operates in bottoms temperature range of about 225 to about 275° C. and an overhead pressure of about 250 to about 350 kPa (gauge).

The non-normal paraffin stream may be isomerized in an isomerization unit 150 to increase its concentration of normal paraffins. Reactions that promote the production of normal paraffins include iso-paraffin disproportionation reactions, ring saturation, opening of aromatics and cyclics, reverse isomerization of iso-paraffins, and paraffin hydrocracking reactions. Cracking of some of the paraffins can occur in the isomerization unit 150 to produce C4− paraffins. It is believed that the paraffin disproportionation reactions occur by the combination of two iso-paraffins followed by scission into one lighter paraffin and one heavier paraffin. For example, two isopentanes can combine and form an isobutane and an isohexane in the presence of hydrogen. The isobutanes can further react via disproportionation to form a propanes and isopentanes. A portion of the produced isobutanes also converts to normal butanes via isomerization reactions. Production of normal propane and butane via disproportionation and isomerization reactions occurs with low production of low-value undesired methane as a cracked product. In the isomerization unit 150, hydrocracking of isopentane and/or isohexane occurs to produce methane, ethane, propane, and isobutane. The isobutane can further react via disproportionation reactions and/or isomerization to further produce normal paraffins. Thus, there is an increase in the overall yield of the normal paraffins in the isomerization unit 150.

The net raffinate overhead stream in the net raffinate overhead line 132 characterized as a low paraffin stream should be isobutane rich and comprise less than about 5 to about 10 mol % pentanes. The low paraffin stream comprising an isobutane stream in the net raffinate overhead line 132 may be combined with a low hydrogen stream in a low hydrogen line 152 and heated by heat exchange with a low isomerate stream in line 159 and fed to a low isomerization unit 154 in a low isomerization feed stream in a low isomerization feed line 156. If chlorided alumina catalyst is used as the low isomerization catalyst, a chloriding agent in line 153 will be added to the low isomerization feed stream in line 156.

The low isomerization unit 154 may be operated under low isomerization conditions because lower paraffins are in the low isomerization feed stream. In the low isomerization unit 154, isobutane, in the presence of hydrogen provided by the low hydrogen line 152 and a low isomerization catalyst, are converted to increase the concentration of normal paraffins: ethane, propane, and normal butane. The low isomerization unit 154 may be in a single reactor 157 or in two or more separate isomerization reactors 157 and 158 with suitable means therebetween to ensure that the desired isomerization temperature is maintained at the entrance to each reactor. A low isomerate stream comprising an increased concentration of normal paraffins exits the last isomerization reactor 159 in the low isomerization unit 154 in a low isomerate line 159.

Similarly, in an embodiment, the optional raffinate side stream in the raffinate side line 135 characterized as a high paraffin stream should be isopentane rich and comprise less than about 5 to about 10 mol % butanes. The high paraffin stream comprising an isopentane stream in the raffinate side line 135 may be combined with a high hydrogen stream in a high hydrogen line 162 and heated by heat exchange with a high isomerate stream in line 170 and fed to a high isomerization unit 160 in a high isomerization feed stream in a high isomerization feed line 166. If chlorided alumina catalyst is used as the high isomerization catalyst, a chloriding agent in line 163 will be added to the low isomerization feed stream in line 166. In an alternative embodiment, the raffinate column 124 may only produce two streams with the overhead stream in line 132 going to a raffinate splitter column (not shown) to produce the low isomerization feed stream in the overhead and the high isomerization feed stream in the bottoms.

The high isomerization unit 160 may be operated under high isomerization conditions because higher paraffins are in the high isomerization feed stream. In the high isomerization unit 160, isopentane and isohexane and naphthenes, such as cyclopentane, methylcyclopentane, cyclohexane and methylcyclohexane, in the presence of hydrogen provided by the high hydrogen line 162 and a high isomerization catalyst, are converted to increase the concentration of normal paraffins: ethane, propane, and normal butane, normal pentane and normal hexane. The high isomerization unit 160 may be in a single reactor 167 or in two or more separate isomerization reactors 167, 168, and 169 with suitable means therebetween to ensure that the desired isomerization temperature is maintained at the entrance to each reactor. A high isomerate stream comprising an increased concentration of normal paraffins exits the last isomerization reactor 169 in the high isomerization unit 160 in a high isomerate line 170.

The isomerization catalyst in the isomerization unit 150 may include chlorided alumina, sulfated zirconia, tungstated zirconia or zeolite-containing isomerization catalysts. The isomerization catalyst may be amorphous, e.g., based upon amorphous alumina, or zeolitic. A zeolitic catalyst would still normally contain an amorphous binder. The catalyst may comprise a sulfated zirconia and platinum as described in U.S. Pat. No. 5,036,035 and EP 0666109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. An advantage of a non-chlorided catalyst, such as a sulfated zirconia catalyst, is the absence of chloride omitting further treatment of the effluent streams from the isomerization unit 150.

The isomerization process conditions in the isomerization reactors include an average reactor temperature usually ranging from about 40° to about 250° C. Isomerization reactor operating pressures generally range from 1 MPa (145 psia) to about 5.5 MPa (800 psia) (g). Liquid hourly space velocities (LHSV) range from about 0.2 to about 25 volumes of hydrocarbon feed per hour per volume of catalyst. Higher hydrogen partial pressure in the high isomerization unit 160 is required to maintain stability of the isomerization catalyst, to saturate and open aromatic and naphthenic rings, to promote hydrocracking reactions and to achieve high conversion to normal paraffins.

Contacting within the isomerization unit 150 may be effected using the isomerization catalyst in a fixed-bed system, a moving-bed system, a fluidized-bed system, or in a batch-type operation. The reactants may be contacted with the bed of high isomerization catalyst particles in upward, downward, or radial-flow fashion. The reactants may be in the liquid phase or in a mixed liquid-vapor phase when contacted with the isomerization catalyst particles, with a mixed phase or vapor phase being preferred.

The reactions in the isomerization unit 150 generate an exotherm across the reactors so the isomerization effluent streams must be cooled between reactors by heat exchange with upstream feed streams. Since hydrocracking reactions are accompanied by hydrogenation reactions that are very exothermic, two to five high isomerization reactors in sequence enable improved control of individual reactor temperatures and partial catalyst replacement without a process shutdown.

The low isomerate stream in the low isomerate line 159 and the high isomerate stream in the high isomerate line 170 may be fed to an isomerate column 172 which may be a depropanizer column in an isomerate column feed line 174. The depropanizer column 172 separates the low and high isomerate streams in the isomerate column feed line 174 into an isomerate overhead stream comprising propane and lighter gases in an overhead line 176 and an isomerate bottoms stream comprising C4+ paraffins in a bottoms line 178.

The isomerate overhead stream is withdrawn from the isomerate column 172 in a isomerate overhead line 176 and condensed in a cooler and passed into a separator 177. A portion of the condensed isomerate overhead stream is recycled to the isomerate column 172 as reflux through a reflux line and the remaining portion of the condensed propane rich stream, is withdrawn in a net isomerate overhead line 180. The isomerate overhead stream in the line 180 comprising ethane and propane may be charged to the steam cracking unit 5 in line 6 or to a paraffin dehydrogenation process (not shown) perhaps after separation of lighter components from the propane. An isomerate off gas stream comprising C2− hydrocarbons and light gases may be taken from the separator overhead in an isomerate off gas line and passed to fuel gas processing or sent to further processing for further recovery of hydrogen and/or ethane which can be used as steam cracking feed to the steam cracking unit 5.

The isomerate bottoms stream is withdrawn from the isomerate column 172 through a bottoms line 178 from which a portion of the isomerate bottoms stream flows through a reboiler line 177, a reboiler heater and returns to the isomerate column 172. The remaining portion of the isomerate bottoms stream flows through a net isomerate bottoms line 179 rich in C4-C7 normal and iso-paraffins. The isomerate column 172 operates in bottoms temperature range of about 90 to about 150° C. and an overhead pressure range of about 1.3 to about 2.7 MPa and preferably about 1.7 to about 2.5 MPa.

In an embodiment, the remaining portion of the isomerate bottoms stream in the net isomerate bottoms line 179 rich in C4-C7 paraffins characterized as a C4+ paraffin stream is heat exchanged with the isomerate column feed stream in line 174 and recycled to the paraffin separation unit 100 through the adsorption feed line 104 to again extract normal paraffins from the isomerate bottoms stream to produce a concentrated normal paraffin extract stream in line 140 for feed to the steam cracking unit 5.

SPECIFIC EMBODIMENTS

While the following is described in conjunction with specific embodiments, it will be understood that this description is intended to illustrate and not limit the scope of the preceding description and the appended claims.

A first embodiment of the disclosure is a process for separating a normal paraffins stream from non-normal paraffins stream comprising separating a feed stream to provide a separator overhead stream rich in methyl cyclopentane or cyclohexane and a separator bottom stream rich in cyclohexane or methylcyclohexane; taking an isomerization feed stream from the separator overhead stream; and isomerizing the isomerization feed stream to provide an isomerate stream. An embodiment of the disclosure is one, any or all of prior embodiments in this paragraph up through the first embodiment in this paragraph wherein taking the isomerization feed stream further comprises separating the separator overhead stream into a normal paraffins stream and a non-normal paraffins stream. An embodiment of the disclosure is one, any or all of prior embodiments in this paragraph up through the first embodiment in this paragraph further comprising steam cracking the normal paraffins stream. An embodiment of the disclosure is one, any or all of prior embodiments in this paragraph up through the first embodiment in this paragraph further comprising separating the isomerate stream into an isomerate overhead stream and an isomerate bottom stream. An embodiment of the disclosure is one, any or all of prior embodiments in this paragraph up through the first embodiment in this paragraph further comprising steam cracking the isomerate overhead stream. An embodiment of the disclosure is one, any or all of prior embodiments in this paragraph up through the first embodiment in this paragraph further comprising recycling the isomerate bottom stream to the step of separating the isomerate bottoms stream into a normal paraffin stream an a non-normal paraffins stream. An embodiment of the disclosure is one, any or all of prior embodiments in this paragraph up through the first embodiment in this paragraph wherein taking the isomerization feed stream further comprises taking the separator overhead stream to provide the isomerization feed stream. An embodiment of the disclosure is one, any or all of prior embodiments in this paragraph up through the first embodiment in this paragraph wherein taking the isomerization feed stream further comprises separating the separator overhead stream into a normal paraffins stream and a non-normal paraffins stream and splitting the non-normal paraffins stream, or splitting the separator overhead stream to provide a low isomerization feed stream as the isomerization feed stream and a high isomerization fed stream and isomerizing the low isomerization feed stream and the high isomerization feed stream separately. An embodiment of the disclosure is one, any or all of prior embodiments in this paragraph up through the first embodiment in this paragraph further comprising saturating aromatics in a steam cracked stream to provide the feed stream. An embodiment of the disclosure is one, any or all of prior embodiments in this paragraph up through the first embodiment in this paragraph further comprising fractionating a saturated aromatics stream from the saturation step into the separator overhead stream comprising the feed stream and a separator bottoms stream and steam cracking the separator bottom stream. An embodiment of the disclosure is one, any or all of prior embodiments in this paragraph up through the first embodiment in this paragraph further comprising stripping the separator overhead stream to provide to provide the feed stream.

A second embodiment of the disclosure is a process for separating a normal paraffins stream from a non-normal paraffins stream comprising separating a feed stream to provide a separator overhead stream rich in methyl cyclopentane or cyclohexane and a separator bottom stream rich in cyclohexane or methylcyclohexane; and separating the separator overhead stream into a normal paraffins stream and a non-normal paraffins stream. An embodiment of the disclosure is one, any or all of prior embodiments in this paragraph up through the second embodiment in this paragraph further comprising isomerizing the non-normal paraffins stream to provide an isomerate stream. An embodiment of the disclosure is one, any or all of prior embodiments in this paragraph up through the second embodiment in this paragraph further comprising steam cracking the normal paraffins stream. An embodiment of the disclosure is one, any or all of prior embodiments in this paragraph up through the second embodiment in this paragraph further comprising separating the isomerate stream into an isomerate overhead stream and an isomerate bottom stream; steam cracking the isomerate overhead stream; and recycling the isomerate bottom stream to the step of separating the isomerate bottoms stream into a normal paraffin stream an a non-normal paraffins stream. An embodiment of the disclosure is one, any or all of prior embodiments in this paragraph up through the second embodiment in this paragraph further comprises isomerizing the separator overhead stream to provide the isomerate stream.

A third embodiment of the disclosure is a process for separating a normal paraffins stream from a non-normal paraffins stream comprising saturating aromatics in a steam cracked stream to provide a feed stream; separating the feed stream to provide a separator overhead stream rich in methyl cyclopentane or cyclohexane and a separator bottom stream rich in cyclohexane or methylcyclohexane; taking an isomerization feed stream from the separator overhead stream; and isomerizing the isomerization feed stream to provide an isomerate stream. An embodiment of the disclosure is one, any or all of prior embodiments in this paragraph up through the third embodiment in this paragraph further comprising fractionating a saturated aromatics stream from the saturation step into separator overhead stream comprising the feed stream and a separator bottoms stream and steam cracking the separator bottom stream. An embodiment of the disclosure is one, any or all of prior embodiments in this paragraph up through the third embodiment in this paragraph wherein taking the isomerization feed stream further comprises separating the separator overhead stream into a normal paraffins stream and a non-normal paraffins stream comprising the isomerization feed stream.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for separating an isomerate stream comprising:
   separating a feed stream to provide a separator overhead stream rich in methyl cyclopentane or cyclohexane and a separator bottom stream rich in cyclohexane or methylcyclohexane;
   taking an isomerization feed stream from said separator overhead stream; isomerizing said isomerization feed stream to provide said isomerate stream;
   separating said isomerate stream into an isomerate overhead stream and an isomerate bottom stream; and
   steam cracking said isomerate overhead stream.

2. The process of claim 1 wherein taking said isomerization feed stream further comprises separating said separator overhead stream into a normal paraffins stream and a non-normal paraffins stream.

3. The process of claim 2 further comprising steam cracking said normal paraffins stream.

4. The process of claim 2 further comprising recycling said isomerate bottom stream to the step of separating the separator overhead stream into a normal paraffin stream and a non-normal paraffin stream.

5. The process of claim 1 wherein taking said isomerization feed stream further comprises taking said separator overhead stream to provide said isomerization feed stream.

6. The process of claim 1 wherein taking said isomerization feed stream further comprises separating said separator overhead stream into a normal paraffins stream and a non-normal paraffins stream and splitting said non-normal paraffins stream, or splitting said separator overhead stream to provide a low isomerization feed stream rich in C4 hydrocarbons as said isomerization feed stream and a high isomerization feed stream rich in C5+ hydrocarbons and isomerizing said low isomerization feed stream and said high isomerization feed stream separately.

7. The process of claim 1 further comprising saturating aromatics in a steam cracked stream to provide said feed stream.

8. The process of claim 7 further comprising separating a saturated aromatics stream from said saturation step as said feed stream into said separator overhead stream and said separator bottom stream and steam cracking said separator bottom stream.

9. The process of claim 8 further comprising stripping said separator overhead stream to provide to provide said feed stream.

10. A process for separating a normal paraffins stream from a non-normal paraffins stream comprising:
    separating a feed stream to provide a separator overhead stream rich in methyl cyclopentane or cyclohexane and a separator bottom stream rich in cyclohexane or methylcyclohexane;
    separating said separator overhead stream into a normal paraffins stream and a non-normal paraffins stream; and
    splitting said non-normal paraffins stream to provide a low isomerization feed stream rich in C4 hydrocarbons and a high isomerization feed stream rich in C5+ hydrocarbons and isomerizing said low isomerization feed stream and said high isomerization feed stream separately.

11. The process of claim 10 further comprising isomerizing said non-normal paraffins stream to provide an isomerate stream.

12. The process of claim 10 further comprising steam cracking said normal paraffins stream.

13. The process of claim 10 further comprising separating said isomerate stream into an isomerate overhead stream and an isomerate bottom stream; steam cracking the isomerate overhead stream; and recycling said isomerate bottom stream to the step of separating the isomerate bottoms stream into a normal paraffin stream and a non-normal paraffins stream.

14. A process for producing an isomerate stream comprising:
    saturating aromatics in a steam cracked stream to provide a feed stream;
    separating said feed stream to provide a separator overhead stream rich in methyl cyclopentane or cyclohexane and a separator bottom stream rich in cyclohexane or methylcyclohexane;
    taking an isomerization feed stream from said separator overhead stream; and
    isomerizing said isomerization feed stream to provide an isomerate stream.

15. The process of claim 14 further comprising fractionating a saturated aromatics stream from said saturation step into separator overhead stream comprising said feed stream and a separator bottoms stream and steam cracking said separator bottom stream.

16. The process of claim 14 wherein taking said isomerization feed stream further comprises separating said separator overhead stream into a normal paraffins stream and a non-normal paraffins stream comprising said isomerization feed stream.

* * * * *